United States Patent
Mahalingam

(10) Patent No.: US 7,993,312 B2
(45) Date of Patent: Aug. 9, 2011

(54) URINARY DEVICE

(76) Inventor: Padmanabhan Mahalingam, Adyar (IN)

( * ) Notice: Subject to any disclaimer, the term of this patent is extended or adjusted under 35 U.S.C. 154(b) by 621 days.

(21) Appl. No.: 12/061,026

(22) Filed: Apr. 2, 2008

(65) Prior Publication Data

US 2008/0262448 A1   Oct. 23, 2008

Related U.S. Application Data

(60) Provisional application No. 60/916,023, filed on May 4, 2007, provisional application No. 60/913,077, filed on Apr. 20, 2007.

(51) Int. Cl.
- *A61F 5/451* (2006.01)
- *A61F 5/455* (2006.01)
- *A47K 11/12* (2006.01)

(52) U.S. Cl. .......................... 604/329; 4/144.3; 600/574

(58) Field of Classification Search .................. 604/329, 604/349, 327–328; 600/574; 4/144.1–144.4
See application file for complete search history.

(56) References Cited

U.S. PATENT DOCUMENTS

| | | | | |
|---|---|---|---|---|
| 1,510,973 A * | 10/1924 | Behan | ............................ | 604/329 |
| 1,928,170 A * | 9/1933 | Dwork | ............................ | 4/144.4 |
| 2,182,254 A * | 12/1939 | Farrell | ............................ | 4/450 |
| 2,522,273 A * | 9/1950 | Johnson | ............................ | 4/144.1 |
| 3,131,403 A * | 5/1964 | Hill | ............................ | 4/144.3 |
| 3,194,238 A * | 7/1965 | Breece, Jr. | ............................ | 604/329 |
| 3,335,714 A * | 8/1967 | Giesy | ............................ | 600/574 |
| 3,349,768 A * | 10/1967 | Keane | ............................ | 604/347 |
| 3,512,185 A * | 5/1970 | Ellis | ............................ | 604/329 |
| 3,528,423 A * | 9/1970 | Lee | ............................ | 604/329 |
| 3,568,218 A * | 3/1971 | Beckman | ............................ | 4/144.1 |
| 3,680,543 A * | 8/1972 | Cox | ............................ | 600/574 |
| 3,776,235 A * | 12/1973 | Ratcliffe et al. | ............................ | 604/329 |
| 3,864,759 A * | 2/1975 | Horiuchi | ............................ | 604/329 |
| 3,995,329 A * | 12/1976 | Williams | ............................ | 4/144.3 |
| 4,164,795 A * | 8/1979 | Johnson | ............................ | 4/144.1 |
| 4,194,508 A * | 3/1980 | Anderson | ............................ | 604/329 |
| 4,198,979 A * | 4/1980 | Cooney et al. | ............................ | 604/329 |
| 4,270,539 A * | 6/1981 | Frosch et al. | ............................ | 604/347 |
| 4,583,983 A * | 4/1986 | Einhorn et al. | ............................ | 604/329 |
| 4,610,675 A * | 9/1986 | Triunfol | ............................ | 604/329 |
| 4,681,572 A * | 7/1987 | Tokarz et al. | ............................ | 604/329 |
| 4,795,449 A * | 1/1989 | Schneider et al. | ............................ | 604/329 |
| 4,846,817 A * | 7/1989 | Mohr et al. | ............................ | 604/329 |
| 4,889,532 A * | 12/1989 | Metz et al. | ............................ | 604/330 |
| 4,889,533 A * | 12/1989 | Beecher | ............................ | 604/330 |
| 4,911,698 A * | 3/1990 | Wapner | ............................ | 604/329 |
| 4,936,838 A * | 6/1990 | Cross et al. | ............................ | 604/329 |
| 5,004,463 A * | 4/1991 | Nigay | ............................ | 604/329 |
| 5,091,998 A * | 3/1992 | Witzke | ............................ | 4/144.4 |
| 5,295,983 A * | 3/1994 | Kubo | ............................ | 604/329 |
| 5,387,205 A * | 2/1995 | Cummins | ............................ | 604/329 |
| 6,123,691 A * | 9/2000 | Karavani et al. | ............................ | 604/329 |

(Continued)

*Primary Examiner* — Jacqueline F. Stephens
*Assistant Examiner* — Paula L Craig
(74) *Attorney, Agent, or Firm* — Donald R. Boys; Central Coast Patent Agency, Inc.

(57) ABSTRACT

A urinary device for use by a person has an elongate tube having an outside wall, an inside wall and a length, a cup for collecting urine, the cup of greater diameter than the tube, formed at a free end of the tube, substantially concentric with the tube, for placing over the person's urethra, and a shield formed about the outside wall of the tube, near the cup, substantially perpendicular to a longitudinal axis of the tube, the shield having a concave surface facing the cup shaped to conform to a user's pubic area.

2 Claims, 4 Drawing Sheets

U.S. PATENT DOCUMENTS

| | | | |
|---|---|---|---|
| 6,151,721 A * | 11/2000 | Whitfield | 4/144.1 |
| 6,183,454 B1 * | 2/2001 | Levine et al. | 604/329 |
| 6,280,425 B1 * | 8/2001 | Del Guercio | 604/327 |
| 6,342,049 B1 * | 1/2002 | Nichols | 604/329 |
| 6,592,560 B2 * | 7/2003 | Snyder | 604/331 |
| 6,719,741 B2 * | 4/2004 | Ching | 604/329 |
| 6,723,078 B1 * | 4/2004 | Pennington et al. | 604/327 |
| 6,814,719 B2 * | 11/2004 | Preston et al. | 604/329 |
| 6,904,621 B2 * | 6/2005 | Otto et al. | 4/144.1 |
| 7,181,781 B1 * | 2/2007 | Trabold et al. | 4/144.4 |
| 7,325,256 B1 * | 2/2008 | Pecinka, Sr. | 4/144.1 |
| 7,435,242 B2 * | 10/2008 | Levinson | 604/329 |
| 2001/0049520 A1 * | 12/2001 | Robertson et al. | 604/544 |
| 2005/0010182 A1 * | 1/2005 | Parks et al. | 604/355 |
| 2006/0005307 A1 * | 1/2006 | Arguelles | 4/144.1 |
| 2008/0028503 A1 * | 2/2008 | Brown | 4/144.1 |

* cited by examiner

URINARY DEVICE

CROSS-REFERENCE TO RELATED APPLICATIONS

The present invention claims priority to a U.S. patent application Ser. No. 60/913,077, filed Apr. 20, 2007, entitled "Feminine Urination Device", and to a U.S. provisional patent application Ser. No. 60/916,023, filed May 4, 2007, entitled "Urination Device"; disclosures of which are incorporated in their entirety at least by reference.

BACKGROUND OF THE INVENTION

1. Field of the Invention

The present invention is in the area of personal devices, and pertains more particularly to a device for enabling women, and in some cases men, to urinate in a standing position with ease.

2. Discussion of the State of the Art

It is well-known that a lady cannot urinate in a standing position like a male can without soiling herself due to the nature of the female external genitalia. Women usually open their legs wide and/or bend forwards with their knees folded and urinate into a larger receptacle behind such as a water closet.

A number of devices have attempted to solve this need. They have all been based on a device whose whole contour matches the body around the external genitalia like a very large funnel. These devices were made large for easy use, but are easily soiled because of sealing devices to prevent the urine from leaking out, and cannot be personalized because of the same reasons, for example, a lady cannot carry it around like when she goes to a movie house, and if the movie house installs such a device a second person cannot use it without washing after the previous person's use. Also, due to varying body sizes, many sizes are required to suit the population.

What is clearly needed is a relatively small, hand-held urinary device that may be carried by a user, such as in a purse, so there is no need for more than one person to share the use of a single device. In some cases such a device may be adapted for either a male or a female to use.

SUMMARY OF THE INVENTION

A problem stated above is that existing female urinary devices are difficult to use and have large funnel like receiving ends that are awkward, promote leakage, and make the device difficult to stow away inconspicuously. The inventor therefore has considered functional elements of a urinary device looking for elements that could be modified to provide a device that could be smaller and easier to stow, but without compromising ease of use of the device.

Every urinary device for females includes a funnel or collector to catch urine and a conduit for carrying the urine away from the user. The inventor realized in an inventive moment that if the collector-end of a urinary device could be provided small enough to just cover the urethra without compromising the ability of the user to successfully orientate the device for use, significant improvement in stow ability of the device might result. The inventor therefore constructed a unique female urinary device with a small collector and a location shield that allowed users to conveniently stow the device while maintaining convenient orientation utility of the device aided by a unique body-conforming shield, and in some cases, a positioning rib. As a result, users were able to use the device inconspicuously without discomfort and without leakage from the device.

Accordingly a urinary device for use by a person is provided, comprising an elongate tube having an outside wall, an inside wall and a length, a cup for collecting urine, the cup of greater diameter than the tube, formed at a free end of the tube, substantially concentric with the tube, for placing over the person's urethra, and a shield formed about the outside wall of the tube, near the cup, substantially perpendicular to a longitudinal axis of the tube. The shield acts as top for a user's fingers.

In one embodiment the device tube is bent at one point along the length by an angle of from one to forty-five degrees. In another embodiment the bend is from ten to thirty degrees. In some embodiments there is an elongate rib formed longitudinally on the outside wall of the tube, spanning and connecting the cup and the shield, and also in some embodiments the inside wall of the tube comprises a longitudinal groove to serve as a gutter for urine in use.

BRIEF DESCRIPTION OF THE DRAWING FIGURES

DETAILED DESCRIPTION

The present invention in one embodiment comprises a relatively small, hand-held device that can go into a handbag. In this embodiment it includes a tube of predetermined size which mates directly with the female external urethral orifice. To compensate for dilation of the orifice during higher discharges, the device in this embodiment has a gutter at the mouth of the collector, which takes the effluent away from the body. Further, in this embodiment the tube has a projection that nests in the vestibule of the vulvae and helps locating. For a feeling of well being to the person, this projection also may engage with the clitoris.

Figure 1:
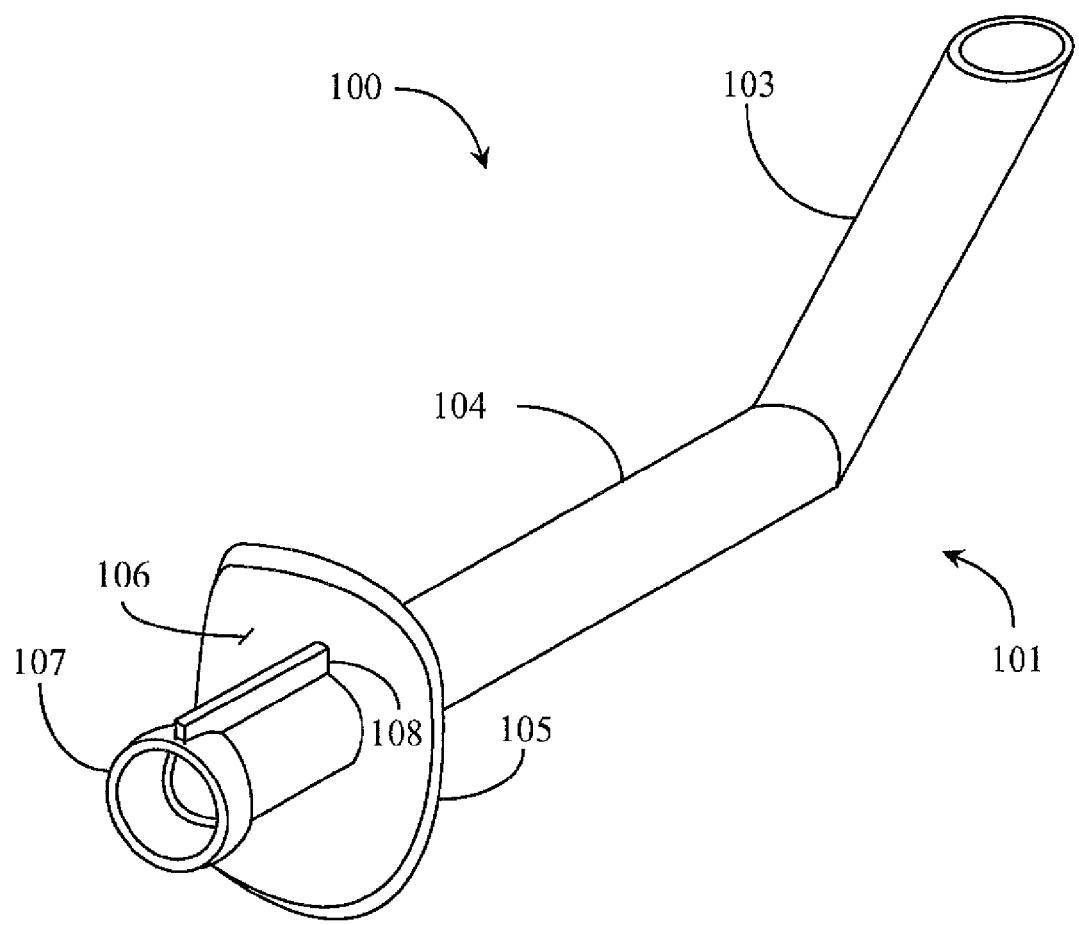
FIG. 1 is a perspective view of a female urinary device according to one embodiment of the invention.

FIG. 1 is a perspective view of a female urinary device 100 according to one embodiment of the invention. Referring now to FIG. 1, the urinary device 100 of the present invention is illustrated in perspective. Device 100 may be manufactured of one material, preferably a durable medical-grade polymer, such as by injection molding. Other rigid and semi-rigid materials may also be used like some metals and ceramics. In one embodiment, device 100 is molded in one piece from medical grade polymer. Device 100 is adapted to be used repeatedly as needed to re-direct urine out and away from the urethra, and may be cleaned and disinfected between uses.

Device 100 in a preferred embodiment includes a conduit or tubing section 101 that is formed or molded to bend at an angle creating tube section 104 and tube section 103. The bend may be relatively abrupt, as shown, or very gradual, in a sweeping curve. Tube section 104 has an annular cup 107, also referred to as a collector, formed on one open end for facilitating a snug fit over the urethra. Cup 107 may be formed on one end of conduit 101 by shaping, molding or flaring before forming the bend creating tube sections 104 and 103, depending on the method of forming or manufacture. In one embodiment, cup 107 may be a separate part that is heat welded, glued or otherwise affixed to the end of tube section 104.

In some embodiments a placement shield 105 is provided on tubing section 104 nearer to cup 107. In this example, shield 105 is positioned over the peripheral wall of tube 104 and may be glued, heat welded or otherwise formed or affixed to the peripheral wall of the tube. In some embodiments a user may manipulate placement shield 105 in order to accurately place device 100 into a suitable position for use. In some embodiments shield 105 may have a concave surface 106 on the side that faces cup 107. An important purpose of the shield is to act as a stop for a user's fingers in use. In some embodiments Shield 105 may also have a crescent-shaped profile that is curved toward cup 107 more so on the lower part of shield 105 than the upper portion of the shield. The combination of the profile of shield 105 and surface 106 provides a naturally conforming surface that conforms to the pubic mound of a user around the urethra to help prevent any leakage that may escape from cup 107.

Shield 105 is strategically positioned away from cup 107 to an amount that facilitates a comfortable fitting of cup 107 over the urethra while the shield rests either against intervening clothing or against the body. The curvature and shape of placement shield 105 may conform to the proximal curvature of the female genital area (pubic mound) or, in other embodiments, may have another shape. A support rib 108 is provided in the embodiment shown on device 100. Support rib 108 bridges the inside of placement shield 105, the top of tube section 104, and cup 107. Support rib 108 is molded, heat welded, or otherwise affixed substantially near the top center portion of the re-directing end of the device. Support rib 108 is not specifically required in order to practice the present invention, but helps a user to locate the urethra by providing an indicator of device position during the act of placing the device over the urethra.

Cup 107 is adapted to encompass or cover the urethra while the user urinates. Holding shield 105 such as with an index and middle finger of one hand holds the device in place against the urethra and the vaginal area surrounding the urethra. In use of the device, the general position and extended direction of tubing section 104 is angularly downward, for example, while a user is standing and using the device while tubing section 103 is presented at a lesser downward angle and away from the user. The exact angle of bend for sections 104 and 103 may vary, generally from zero to about forty-five degrees, however an approximate 10 to 35 degree bend angle is suitable for most users.

While a user is urinating into the device, holding the device in place with one hand, urine is redirected through tube section 104 and tube section 103 and out of the device into a urinal or other selected vessel or urinary target. A user may control the direction of a urine stream by rotating the device slightly clockwise or counter clockwise to vary the direction of tube section 103.

In one embodiment of the present invention, device 100 may be used while the user is fully clothed, as long as there is access to the urethra through one or more layers of clothing, for example, through a zipper opening, or some other opening fabricated in clothing. Also in one embodiment, device 103 may be used during menstrual periods without removing a sanitary shield as long as the shield is adapted with a flap opening of the sort that may be opened to provide access to the urethra.

Device 100 is purposely designed to be relatively small so a person may carry it discretely, for example in a purse or bag. The diameter of the cup and conduit may vary in different embodiments from about one-quarter inch to about one-half inch, and the overall length is from about four to six inches.

Figure 2:
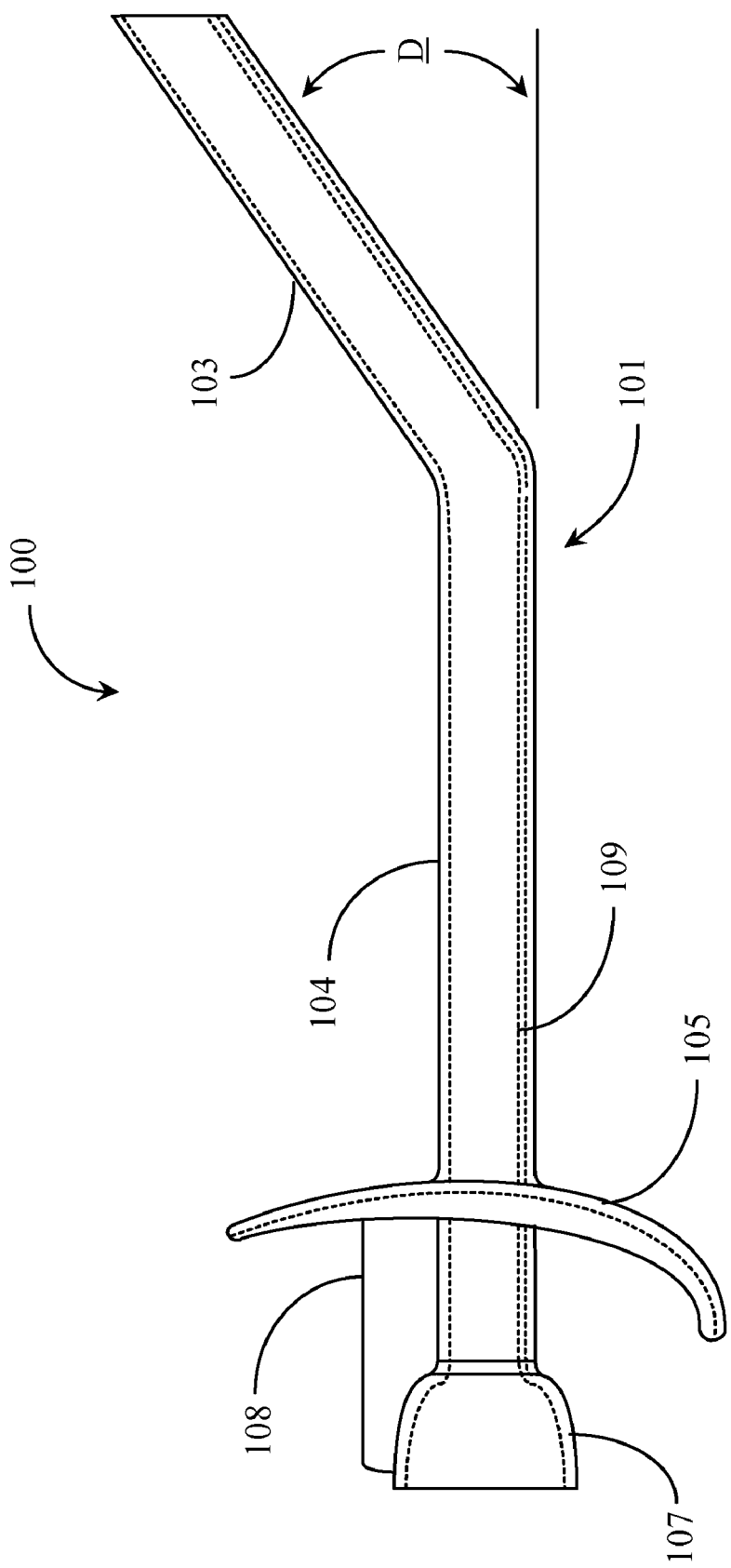
FIG. 2 is a side elevation view of the device of FIG. 1.

FIG. 2 is an elevation view of device 100 of FIG. 1. Conduit section 101 may begin as one section of plastic tubing that is flared or formed at one end to form cup 107 and may be bent to form tubing section 104 and tubing section 103 as shown. Shield 105 and support rib 108 may be provided as separate components that are attached to conduit 101 during a molding process or by some other method such as heat welding, gluing, or the like. Further, in some embodiments, cup 107 may also be a separate attachment so that one device can accommodate cups of different diameters.

The wall thickness for the conduit and for other parts of the device is largely a design choice, and a thickness of 0.1 inch has been found by the inventor to be adequate. The bend angle in device conduit 101 is illustrated herein as an angle D and may vary between zero and forty-five degrees with a nominal preference range of approximately 10 to 35 degrees. Other conduit and cup sizes as well as other angles of bend may be implemented in device 100 without departing from the spirit and scope of the present invention. Device 100 is approximately 6 inches in overall tubing length with approximately 4 inches for tubing section 104 and approximately 2 inches for tubing section 103. The exact lengths of tubing sections 104 and 103 as well as the overall length of device 100 may vary without departing from the spirit and scope of the invention.

In one embodiment of the invention, device 100 may include a gutter 109 formed on the bottom center of the device tubing, the gutter extending into the cup. The gutter may be provided as part of a molding process to help train the urine through the device faster than otherwise would be the case with a round tube.

Figure 3:
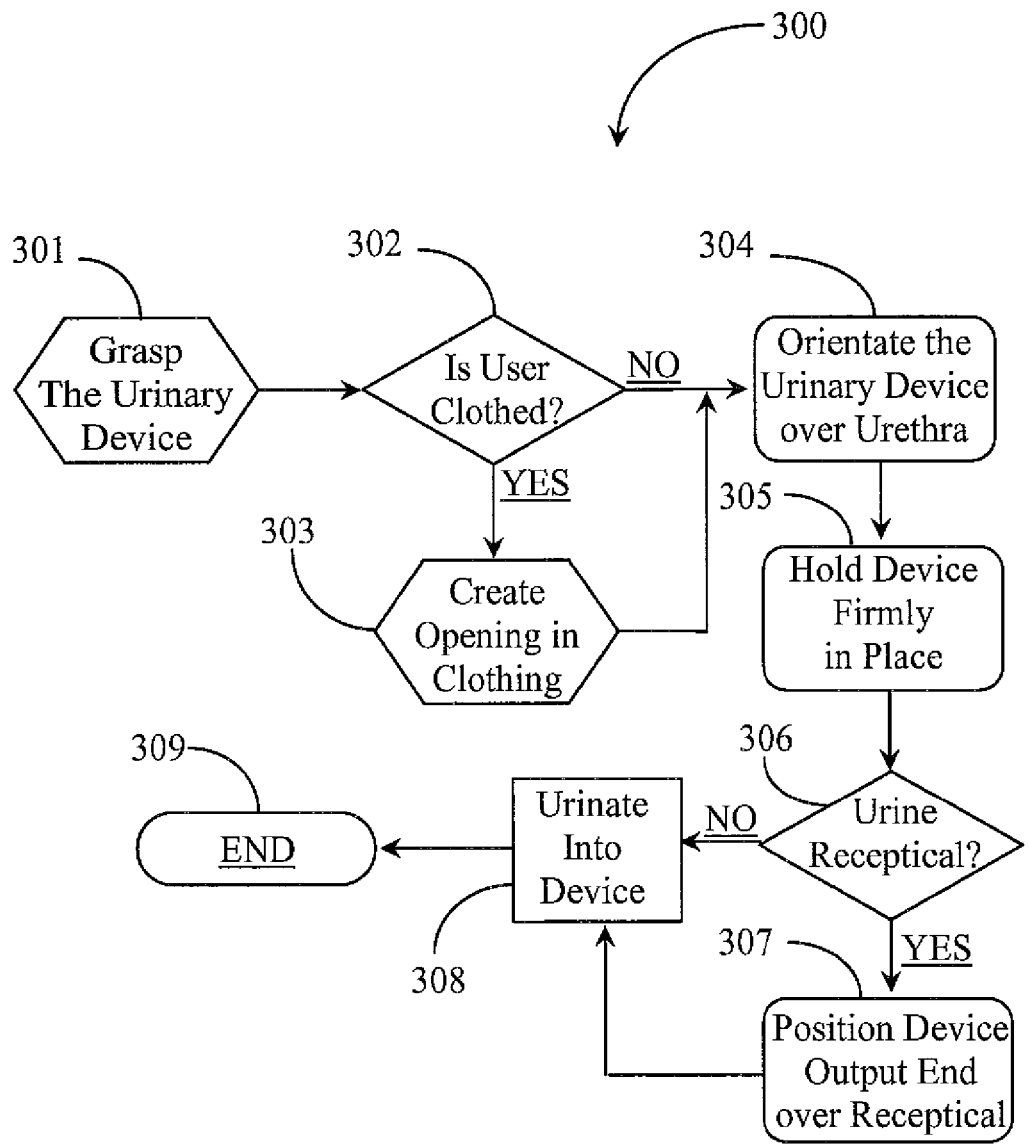
FIG. 3 is a process flow chart illustrating steps 300 for practicing the invention.

FIG. 3 is a process flow chart 300 illustrating steps for practicing the invention. At step 301 a user grasps the urinary device. At step 302 the process branches according to whether or not the user is clothed when using the device. If the user is not clothed at step 302, then the process moves to step 304 where the user orientates the device over the urethra before urinating. If the user is clothed at step 302, the process branches to step 303 where the user creates an opening in the clothing such as by unzipping trousers or the like to provide access to the urethra.

At step 304 the user orientates the device over the urethra aided by the natural curvature of the shield of the device and the position indicator rib (108) if provided. At step 305 the user holds the device firmly in place, the cup covering the urethra and the shield resting against the user.

At step 306, it is determined if the user is using a urine receptacle such as a toilet. If there is a urine receptacle that the user desires to evacuate urine into, the user positions the device output end over the receptacle at step 307 while still firmly holding the device in place over the urethra. At step 308 the user urinates into the device. If at step 306 there is no receptacle, for example, the user is outdoors in the field, the process moves directly to step 308 where the user urinates into the device. At step 308 the user remains in a standing position. At step 309 the process ends. The user may rinse the device after use and stow the device away in a case or plastic bag provided and adapted for the purpose.

In one embodiment, a version of device 100 may be provided with an enlarged conical cup in place of cup 107 so that the device may accommodate a man's genitalia. Such an enlarged cup may be shaped appropriately to accommodate the user while in either a flaccid or erect state. In one embodiment, device 100 may be provided with two separate attachment cups, one for a female such as cup 107 and a larger cup for a male. In still another embodiment, tubing 101 may be telescopic in nature so that the overall length of device 101 may be collapsed for more convenient carrying and then extended to an appropriate length for use.

In the case of a device 100 that is meant to accommodate both men and women, shield 105, used to provide and interface for a woman to manipulate the device is not required in a version of the device adapted for men using a larger cup attachment. Therefore, in one embodiment, shield 105 may be detached from the urinary device. Likewise, cup 107 may be a separate attachment.

Figure 4:
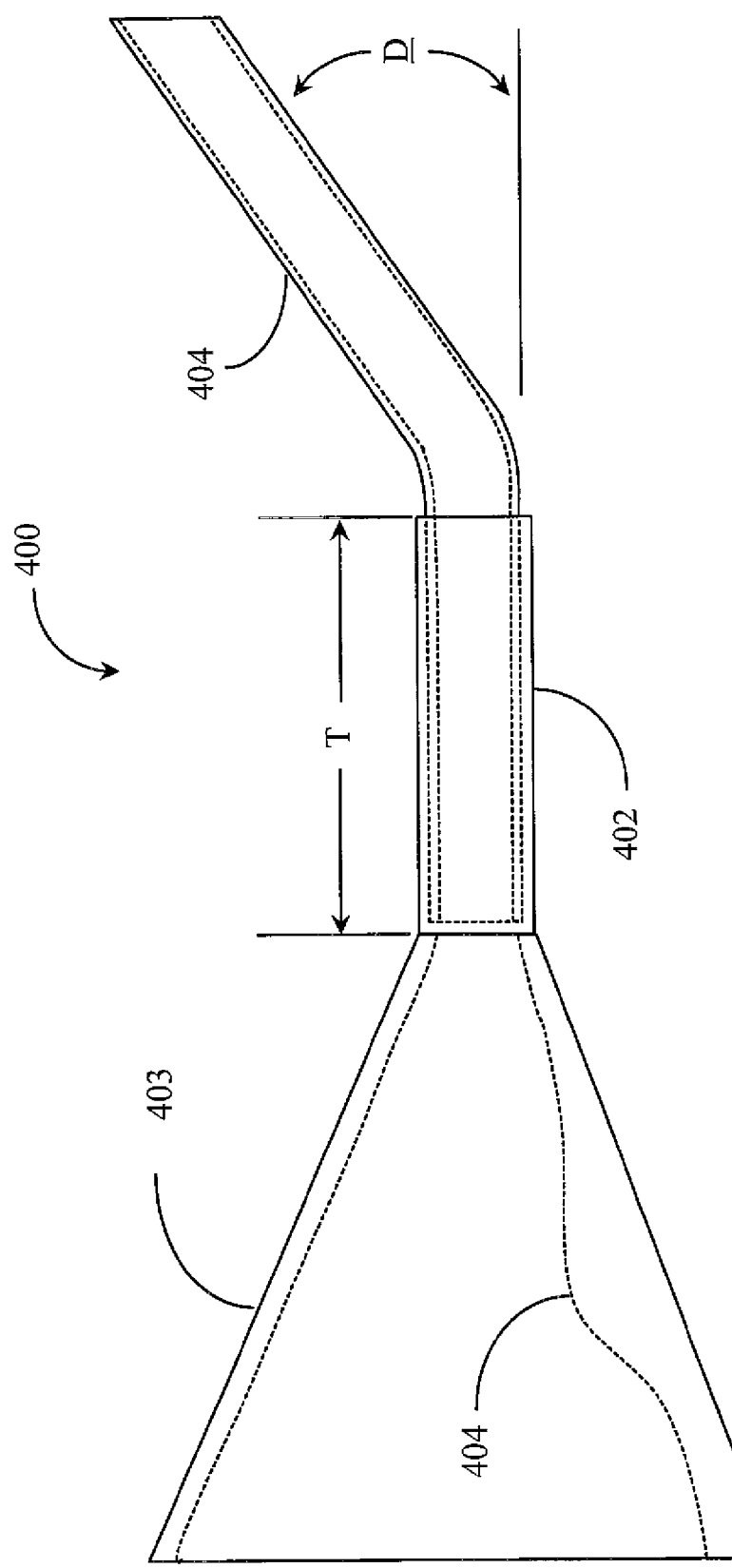
FIG. 4 is an elevation view of a urinary device according to another embodiment of the present invention.

FIG. 4 is an elevation view of a telescopic urinary device 400 with a male attachment. Device 400 comprises a tubing section 404 of a specific diameter and a tubing section 402 having a specific diameter just larger than the diameter of section 404 to provide for telescopic assembly and use. Device 400 may be telescopically collapsed when not in use. A length T illustrates a length defining the added or retracted length of device 400.

In this example, device 400 as a male attachment cup 403 that can be used in place of cup 107 in an embodiment where device 400 can be used by a male or a female. Cup 403 is in the general shape of a cone and may be formed using a molding process. The conical shape of cup 403 should not be construed as a limitation. Cup 403 may also be generally cylindrical in shape. Cup 403 may have a shaped wall 404 provided thereto to conform to a male anatomy, specifically testicular anatomy. A formed portion of cup 403 such as wall 404 may serve to add a level of comfort to the user and to help prevent splash back of urine while in use. Device 400 may also include a gutter as described further above for device 100.

Device 400 may be configured back into a female urination device by removing cup 403 and adding the female cup attachment 107 and the other attachments like the shield and the support rib if provided.

It will be apparent to one with skill in the art that the urinary device of the invention may be provided using some or all of the mentioned features and components without departing from the spirit and scope of the present invention. It will also be apparent to the skilled artisan that the embodiments described above are exemplary of inventions that may have far greater scope than any of the singular descriptions. There may be many alterations made in the descriptions without departing from the spirit and scope of the present invention.

What is claimed is:

1. A urinary device for use by a person, comprising:
    a rigid elongate tube having an outside wall, an inside wall and an overall length;
    a cup for collecting urine, the cup of greater diameter than the tube, formed at a free end of the tube, substantially concentric with the tube, for placing over the person's urethra;
    a shield formed about the outside wall of the tube, near the cup, substantially perpendicular to a longitudinal axis of the tube, the shield having a concave surface facing the cup shaped to conform to a user's pubic area; and
    an elongate rib formed longitudinally on the outside wall of the tube, the rib spanning and connecting the cup and the shield;
    wherein the overall tube length comprises a first and a second rigid section joined at a bend angle of from ten to thirty degrees at one point along the length, and the shield is distanced from the cup so as to position the cup over the urethra.

2. The urinary device of claim 1 wherein the inside wall of the tube comprises a longitudinal groove along the bottom center of the tube to serve as a gutter for channeling urine flow through the tube while the urinary device is in use.

\* \* \* \* \*